US00PP15314P2

(12) United States Plant Patent
Kester

(10) Patent No.: US PP15,314 P2
(45) Date of Patent: Nov. 16, 2004

(54) ***CHRYSANTHEMUM* PLANT NAMED 'FIGRAND SPLENDID'**

(50) Latin Name: *Chrysanthemum×morifolium*
Varietal Denomination: Figrand Splendid

(75) Inventor: Jozef A. J. Kester, De Lier (NL)

(73) Assignee: Fides Goldstock Breeding B.V., DeLier (NL)

( * ) Notice: Subject to any disclaimer, the term of this patent is extended or adjusted under 35 U.S.C. 154(b) by 0 days.

(21) Appl. No.: 10/770,221

(22) Filed: Feb. 2, 2004

(51) Int. Cl.[7] ..... A01H 5/00

(52) U.S. Cl. ..... Plt./286

(58) Field of Search ..... Plt./286

*Primary Examiner*—Anne Marie Grunberg
(74) *Attorney, Agent, or Firm*—C. A. Whealy

(57) ABSTRACT

A new and distinct cultivar of cut flower *Chrysanthemum* plant named 'Figrand Splendid', characterized by its upright growth habit; freely flowering habit; daisy-type inflorescences; attractive light red purple-colored ray florets; green-colored disc florets; response time about 50 days when grown at 18° C.; dark green-colored foliage; strong flowering stems and peduncles; and good postproduction longevity with inflorescences and foliage maintaining good substance and color for about two weeks in an interior environment.

1 Drawing Sheet

Botanical classification/cultivar designation: *Chrysanthemum×morifolium* cultivar Figrand Splendid.

BACKGROUND OF THE INVENTION

The present invention relates to a new and distinct cultivar of cut flower *Chrysanthemum* plant, botanically known as *Chrysanthemum×morifolium* and hereinafter referred to by the name 'Figrand Splendid'.

The new *Chrysanthemum* is a naturally-occurring whole plant mutation of *Chrysanthemum×morifolium* cultivar Figrand Pink, not patented. The cultivar Figrand Splendid was discovered and selected by the Inventor as a single flowering plant within a population of plants of the cultivar Figrand Pink in a controlled environment in De Lier, The Netherlands in May, 2001. The selection of this plant was based on its unique inflorescence coloration.

Asexual reproduction of the new *Chrysanthemum* by vegetative tip cuttings in a controlled environment in De Lier, The Netherlands since August, 2001, has shown that the unique features of this new *Chrysanthemum* are stable and reproduced Figrand Splendid to type in successive generations.

SUMMARY OF THE INVENTION

Plants of the cultivar Figrand Splendid have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Figrand Splendid'. These characteristics in combination distinguish 'Figrand Splendid' as a new and distinct cultivar:

1. Upright cut *Chrysanthemum* that is usually grown as a natural spray.
2. Freely flowering habit, about 15 inflorescences per flowering stem.
3. Daisy-type inflorescences.

4. Attractive light red purple-colored ray florets and green-colored disc florets.
5. Response time about 50 days when grown at 18° C.
6. Dark green-colored foliage.
7. Strong flowering stems and peduncles.
8. Good postproduction longevity with inflorescences and foliage maintaining good substance and color for about two weeks in an interior environment.

Plants of the new *Chrysanthemum* can be compared to plants of the parent, the cultivar Figrand Pink. In side-by-side comparisons conducted in De Lier, The Netherlands, plants of the new *Chrysanthemum* differed primarily from plants of the cultivar Figrand Pink in ray floret coloration as plants of the cultivar Figrand Pink had light purple-colored ray florets.

Plants of the new *Chrysanthemum* can also be compared to plants of the *Chrysanthemum×morifolium* cultivar Splendid Reagan, disclosed in U.S. Plant Pat. No. 10,205. In side-by-side comparisons conducted in De Lier, The Netherlands, plants of the new *Chrysanthemum* differed from plants of the cultivar Splendid Reagan in the following characteristics:

1. Flowering stems of plants of the new *Chrysanthemum* were stronger than flowering stems of plants of the cultivar Splendid Reagan.
2. Plants of the new *Chrysanthemum* had smaller leaves than plants of the cultivar Splendid Reagan.
3. Plants of the new *Chrysanthemum* flowered about four days earlier than plants of the cultivar Splendid Reagan.
4. Plants of the new *Chrysanthemum* were more resistant to White Rust than plants of the cultivar Splendid Reagan.

Plants of the new *Chrysanthemum* can also be compared to plants of the *Chrysanthemum×morifolium* cultivar Kingfisher, disclosed in U.S. Plant Pat. No. 11,497. In side-by-side comparisons conducted in De Lier, The Netherlands, plants of the new *Chrysanthemum* differed from plants of the cultivar Kingfisher in the following characteristics:

1. Flowering stems of plants of the new *Chrysanthemum* were stronger than flowering stems of plants of the cultivar Kingfisher.
2. Plants of the new *Chrysanthemum* had smaller leaves than plants of the cultivar Kingfisher.
3. Plants of the new *Chrysanthemum* had larger inflorescences than plants of the cultivar Kingfisher.

BRIEF DESCRIPTION OF THE PHOTOGRAPH

The accompanying colored photograph illustrates the overall appearance of the new *Chrysanthemum*, showing the colors as reasonably possible to obtain in colored reproductions of this type. Colors in the photograph may differ slightly from the color values cited in the detailed botanical description which accurately describe the colors of the new *Chrysanthemum*.

The photograph comprises a side perspective view of a typical flowering stem of 'Figrand Splendid' grown as a natural spray.

DETAILED BOTANICAL DESCRIPTION

The aforementioned photograph and following observations and measurements describe plants grown in De Lier, The Netherlands, under conditions which approximate commercial practice in a glass-covered greenhouse in June. Cuttings were planted in ground beds and received two weeks of long day/short nights followed by short day/long nights until flowering. Plants were grown as single-stem natural spray cut *Chrysanthemums*. During the production of the flowering plants, day and night temperatures averaged 18.5° C. The photograph and botanical description were taken about ten weeks after planting. In the following description, color references are made to The Royal Horticultural Society Colour Chart, 2001 Edition, except where general terms of ordinary dictionary significance are used.

Botanical classification: *Chrysanthemum×morifolium* cultivar Figrand Splendid.

Commercial classification: Daisy-type cut flower *Chrysanthemum*.

Parentage:

*Female or seed parent.*—*Chrysanthemum×morifolium* cultivar Figrand Pink, not patented.

*Male or pollen parent.*—Proprietary *Chrysanthemum×morifolium* selection identified as code number 748A 1, not patented.

Propagation:

*Type.*—Vegetative tip cuttings.

*Time to initiate roots.*—Summer: About five days at temperatures of 20° C. Winter: About six days at temperatures of 20° C.

*Time to produce a rooted young plant.*—Summer: About 11 days at temperatures of 20° C. Winter: About 15 days at temperatures of 20° C.

*Root description.*—Fine, fibrous and white in color.

*Rooting habit.*—Freely branching.

Plant description:

*Appearance/growth habit.*—Herbaceous daisy-type cut flower that is typically grown as a natural spray. Narrow columnar; moderately vigorous to vigorous.

*Flowering stem description.*—Aspect: Erect. Length: About 78 cm. Diameter (natural spray diameter): About 21 cm. Diameter: About 8 mm. Internode length: About 2.1 cm. Texture: Pubescent; longitudinally ridged. Strength: Strong. Color: Between 137C and 143A.

*Foliage description.*—Arrangement: Alternate; single. Length: About 9.8 cm. Width: About 6.4 cm. Apex: Broadly acute. Base: Attenuate. Margin: Palmately lobed; sinuses parallel to convergent. Texture, upper and lower surfaces: Sparsely pubescent; slightly rough. Color: Developing foliage, upper surface: 137A. Developing foliage, lower surface: 137C to 137D. Fully expanded, upper surface: Slightly darker than 137A. Fully expanded, lower surface: 137C. Venation, upper and lower surfaces: 138B. Petiole: Length: About 1.5 cm. Diameter: About 3.5 mm. Color, upper and lower surfaces: 137D.

Flowering description:

*Appearance.*—Daisy-type inflorescence form with obovate-shaped ray florets. Inflorescences borne on terminals, arising from leaf axils. Disc and ray florets develop acropetally on a capitulum.

*Flowering response.*—Under natural conditions, plant flower mid-October to early November in The Netherlands. At other times of the year, inflorescence initiation and development can be induced under short day/long night conditions (at least 13.5 hours of darkness). Plants exposed to two weeks of long day/short night conditions after planting followed by photoinductive short day/long night conditions flower about 50 days later when grown as a natural spray.

*Postproduction longevity.*—In an interior environment, inflorescences and foliage will maintain good color and substance for about two weeks in an interior environment.

*Quantity of inflorescences.*—Freely flowering habit, about 15 inflorescences per flowering stem.

*Inflorescence size.*—Diameter: About 6.7 cm. Depth (height): About 3.4 cm. Disc diameter: About 1.8 cm. Receptacle diameter: About 2 cm. Receptacle height: About 7 mm.

*Inflorescence buds.*—Shape: Oblate. Height: About 6 mm. Diameter: About 8 mm. Color: Between 137B and 143A.

*Ray florets.*—Shape: Obovate. Length: About 3.1 cm. Width: About 1.4 cm. Apex: Broadly acute. Base: Attenuate. Texture: Smooth, glabrous; longitudinally ridged. Aspect: Initially upright; when fully expanded horizontal to about 20° from horizontal. Number of ray florets per inflorescence: About 24 arranged in three rows. Color: When opening, upper surface: 70A. When opening, lower surface: 76A. Fully opened, upper surface: Close to N74C to N74D. Fully opened, lower surface: 76B to 77D.

*Disc florets.*—Arrangement: Massed at center of receptacle. Shape: Tubular, elongated. Apex: Five-pointed. Length: About 5.5 mm. Width: Apex: About 1.5 mm. Base: About 1 mm. Number of disc florets per inflorescence: About 200. Color: Immature: 150D; towards the apex, 150A. Mature: Apex: 151A to 151B. Mid-section and base: 150D.

*Phyllaries.*—Quantity per inflorescence: About 16. Length: About 1.1 cm. Width: About 4 mm. Shape: Ovate. Apex: Obtuse. Base: Broadly cuneate. Margin: Entire. Texture, upper and lower surfaces: Densely pubescent. Color, upper surface: 143A to 143B. Color, lower surface: Between 137B and 143A to 143B.

*Peduncles.*—Length: First peduncle: About 7.3 cm. Fourth peduncle: About 11.1 cm. Seventh peduncle:

About 13.2 cm. Diameter: About 3 mm. Angle: About 35° from vertical. Strength: Strong. Texture: Densely pubescent. Color: 138A to 138B.

*Reproductive organs.*—Androecium: Present on disc florets only. Anther color: 153B. Pollen amount: Scarce. Pollen color: 12A. Gynoecium: Present on both ray florets. Stigma color: 13A to 13B. Ovary color: 145B.

*Seed/fruit.*—Seed and fruit production has not been observed.

Disease/pest resistance: Plants of the new *Chrysanthemum* have been observed to be resistant to White Rust. Resistance to other pathogens and pests common to *Chrysanthemums* has not been observed on plants grown under commercial conditions.

Temperature tolerance: Plants of the new *Chrysanthemum* have demonstrated good tolerance to low temperatures of 10° C. and high temperatures of 35° C.

It is claimed:

1. A new and distinct cultivar of cut flower *Chrysanthemum* plant named 'Figrand Splendid', as illustrated and described.

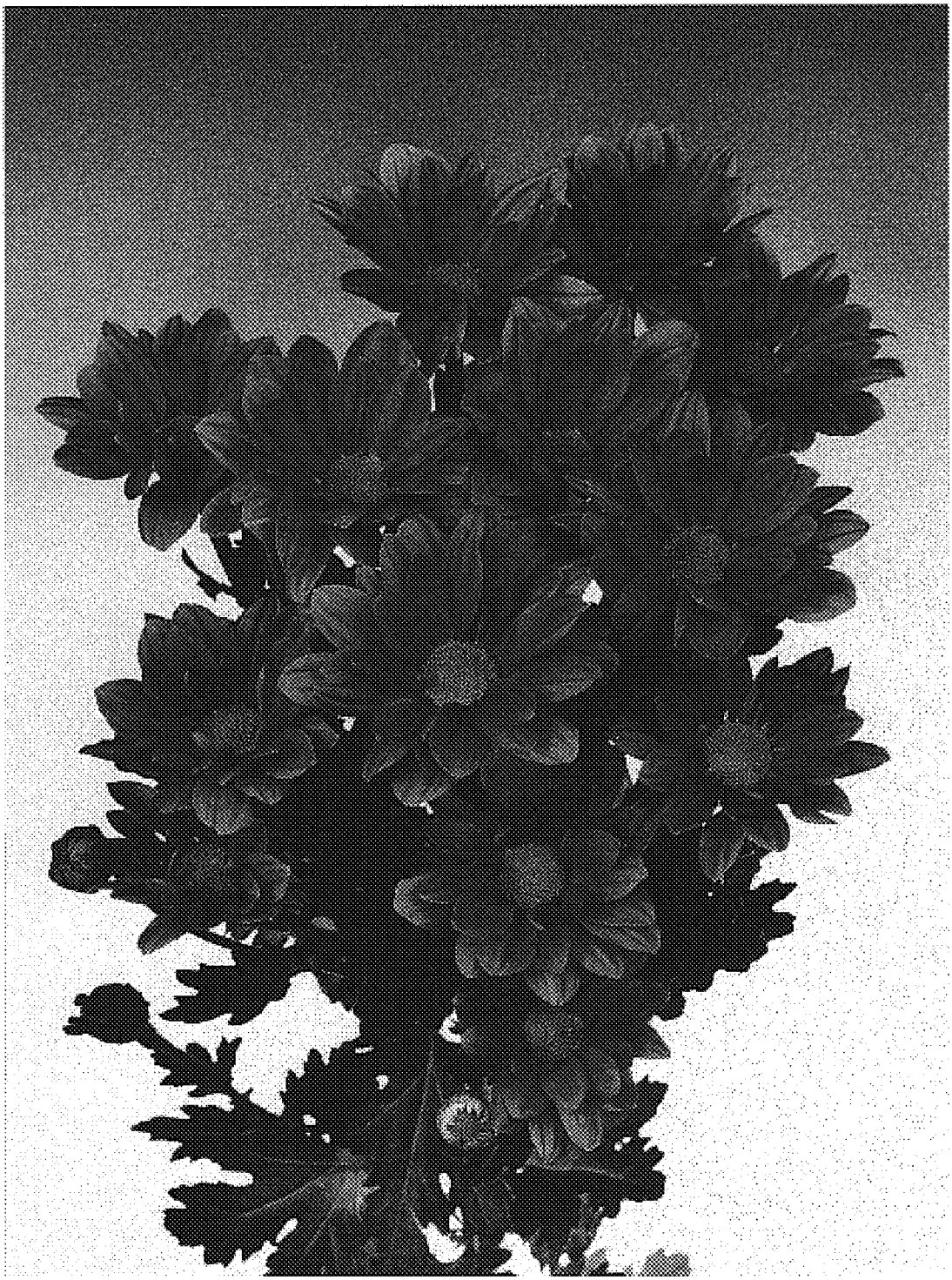

* * * * *